US011306334B2

(12) United States Patent
Haas et al.

(10) Patent No.: US 11,306,334 B2
(45) Date of Patent: Apr. 19, 2022

(54) PROCESS OF PRODUCING OMEGA-HYDROXYL FATTY ACID FROM ALKANE (71) Applicant: Evonik Operations GmbH, Essen (DE)

(72) Inventors: Thomas Haas, Muenster (DE); Markus Poetter, Muenster (DE); Li Li, Shanghai (CN); Guoqing Tao, Shanghai (CN); Dong Cao, Bazhong (CN)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/320,150

(22) PCT Filed: Jul. 26, 2017

(86) PCT No.: PCT/CN2017/094422
§ 371 (c)(1),
(2) Date: Jan. 24, 2019

(87) PCT Pub. No.: WO2018/019245
PCT Pub. Date: Feb. 1, 2018

(65) Prior Publication Data
US 2020/0024624 A1    Jan. 23, 2020

(30) Foreign Application Priority Data
Jul. 26, 2016    (WO) .............. PCT/CN2016/091686

(51) Int. Cl.
*C12P 7/64*    (2006.01)
*C12N 1/16*    (2006.01)
*C12P 7/6409*    (2022.01)

(52) U.S. Cl.
CPC .............. *C12P 7/6409* (2013.01); *C12N 1/16* (2013.01); *C12N 2500/30* (2013.01); *C12Y 103/01034* (2013.01); *C12Y 203/01016* (2013.01); *C12Y 402/01017* (2013.01)

(58) Field of Classification Search
None
See application file for complete search history.

(56) References Cited

U.S. PATENT DOCUMENTS

| | | | |
|---|---|---|---|
| 5,254,466 A | 10/1993 | Picataggio et al. | |
| 7,923,598 B2 | 4/2011 | Meesapyodsuk et al. | |
| 8,597,923 B2 | 12/2013 | Ness et al. | |
| 9,359,581 B2 | 6/2016 | Ness et al. | |
| 2009/0031454 A1 | 1/2009 | Meesapyodsuk et al. | |
| 2009/0054610 A1 | 2/2009 | Gross et al. | |
| 2010/0285545 A1* | 11/2010 | Gross ............. | C12P 7/6427 435/134 |
| 2010/0291653 A1 | 11/2010 | Ness et al. | |
| 2013/0267012 A1* | 10/2013 | Steen ............. | C12N 15/81 435/254.21 |
| 2015/0094483 A1 | 4/2015 | Ness et al. | |
| 2015/0218486 A1 | 8/2015 | Ness et al. | |
| 2016/0298145 A1 | 10/2016 | Laplaza et al. | |
| 2016/0304913 A1* | 10/2016 | Gatter ............. | C12P 7/6427 |
| 2019/0010524 A1 | 1/2019 | Laplaza et al. | |

FOREIGN PATENT DOCUMENTS

| | | |
|---|---|---|
| CN | 101225411 A | 7/2008 |
| CN | 102952774 A | 3/2013 |
| EP | 0 499 622 A1 | 8/1992 |
| IN | 187718 B | 6/2002 |
| JP | 2012-500026 A | 1/2012 |
| JP | 2016-501040 A | 1/2016 |
| WO | WO 2007/147256 A1 | 12/2007 |
| WO | WO 2010/022200 A1 | 2/2010 |
| WO | WO 2014/100461 A2 | 6/2014 |
| WO | WO2015086684 * | 6/2015 |

OTHER PUBLICATIONS

Kizer et al. Appl Environ Microbiol. May 2008;74(10):3229-41. (Year: 2008).*
Prather et al. Curr Opin Biotechnol. Oct. 2008;19(5):468-74. (Year: 2008).*
WO2015086684. Jun. 18, 2015. English Translation (Year: 2015).*
Extended European Search Report dated Mar. 10, 2020 in Patent Application No. 17833548.5, 6 pages.
International Search Report dated Nov. 1, 2017 in PCT/CN2017/094422 filed Jul. 26, 2017, 3 pages.
Stephen Picataggio, et al. "Metabolic Engineering of Candida Tropicalis for the Production of Long-Chain Dicarboxylic Acids" Bio/Technology, vol. 10, No. 8, Aug. 31, 1992, pp. 894-898 and cover page.

* cited by examiner

*Primary Examiner* — Christian L Fronda
(74) *Attorney, Agent, or Firm* — Oblon, McClelland, Maier & Neustadt, L.L.P.

(57) ABSTRACT

Provided is a method of producing at least one omega-hydroxyl fatty acid, the method comprising: (a) contacting at least one alkane with at least one recombinant yeast cell in an aqueous medium, wherein the yeast cell is capable of oxidising the alkane to the corresponding omega-hydroxyl fatty acid and the yeast cell comprises a reduced fatty acid degradation capacity.

17 Claims, 3 Drawing Sheets

PROCESS OF PRODUCING OMEGA-HYDROXYL FATTY ACID FROM ALKANE

FIELD OF THE INVENTION

The present invention relates to a biotechnological method for producing at least one ω-functionalized carboxylic acid from at least one alkane. In particular, the method may use a yeast cell in the presence of acetate to produce the corresponding ω-hydroxyl carboxylic acid and/or ester thereof from at least one alkane.

BACKGROUND OF THE INVENTION

ω-hydroxyl fatty acids are very valuable monomers, which can be used to synthesize a unique family of polyethylene-like bio-based plastics. Currently, ω-hydroxyl fatty acids are produced mainly by chemical means which require expensive catalysts and harsh conditions. Accordingly, biotechnological means of producing ω-hydroxyl fatty acids are preferred.

There are several biotechnological means of producing ω-hydroxyl fatty acids and/or esters thereof that are known in the art. For example, genetically modified cells that are capable of producing ω-functionalized carboxylic acids from carboxylic acid used as a substrate has been previously described at least in WO2009077461 and EP2322598. A very similar procedure is described in WO2011008232 using *Candida* cells where the β-oxidation pathway is blocked in the cells, and co-functionalized carboxylic acids were formed from fatty acid used as a substrate. These methods have the disadvantage of using fatty acids as the starting material. This is because, the fatty acids and derivatives thereof used are mainly obtained exclusively from plant and animal oils or fats. Animal fats as raw materials still meet little client acceptance and plant oils which contain short- and middle-length fatty acids are either difficult to obtain or are produced only in tropical regions (result of destruction of rainforest). Further, particular plant and animal oil or fat raw materials have specific, but defined fatty acid profiles resulting in coupled production.

WO2013024114 discloses a method of producing w-functionalized carboxylic acids and/or esters thereof, including ω-hydroxyl fatty acids from simple carbon sources (such as glucose, saccharose, arabinose, xylose, lactose, fructose, maltose, molasses, starch, cellulose and hemicellulose, but also glycerin or very simple organic molecules such as $CO_2$, CO or synthesis gas). These simple sugars especially glucose are usually more expensive to obtain. The method of producing ω-hydroxyl fatty acids and/or esters thereof from simple carbon sources may also be considered complicated as the cells used in this method have to be genetically modified to increase production of carboxylic acids from these simple carbon sources first. This thus increases the cost of production.

*Candida cloacae* and *Candida tropicalis* were found to be able to grow with alkanes as the only carbon source. For example, *Candida tropicalis* is able to oxidize middle to long chain alkanes, to synthesize dicarboxylic acids. The synthesized dicarboxylic acids are then known to be degraded through β-oxidation pathway. In *Candida tropicalis* with blocked or inhibited β-oxidation pathway, dicarboxylic acids are always the main product and a very small amount of ω-hydroxyl fatty acids are produced at low selectivity.

There is thus a need in the art for an environmentally friendly, simple and sustainable method to produce ω-hydroxyl fatty acids from carbon sources besides fatty acids and/or simple carbon.

DESCRIPTION OF THE INVENTION

The present invention provides a method of oxidising at least one alkane wherein the method is a biocatalytic method that may be carried out in the presence of acetate. In particular, the acetate may be used as a co-substrate for the oxidising of the alkane to produce at least one ω-hydroxyl fatty acid. The use of these genetically modified cells in a method to produce ω-hydroxyl fatty acid from alkanes may add flexibility to the production of these compounds by enabling the use of a readily available alternative petrochemical raw materials for its production. Also, the use of whole-cell biocatalysts capable of integrating the entire means of converting alkanes to ω-hydroxyl fatty acid within them, makes the process of conversion simpler as only a small number of process steps are involved in the conversion. The reliance of ω-hydroxyl fatty acid production on commonly used expensive carbon substrates such as fatty acids may also be eliminated.

The present invention provides a method of producing at least one omega-hydroxyl fatty acid from at least one carbon substrate, wherein the method comprises:

(a) contacting the carbon substrate with at least one yeast cell in an aqueous medium, wherein the yeast cell is capable of oxidising the carbon substrate to the corresponding omega-hydroxyl fatty acid and/or dicarboxylic acid; and the yeast cell comprises a reduced fatty acid degradation capacity, wherein the aqueous medium comprises at least one $C_1$ to $C_4$ organic compound.

In particular, the reduced fatty acid degradation capacity may be a result of
  (i) a decrease in expression relative to the wild type cell of at least one enzyme involved in the beta-oxidation pathway; and/or
  (ii) at least one loss-of-function mutation in at least one enzyme involved in the beta-oxidation pathway.

The $C_1$ to $C_4$ organic compound may be used as a co-substrate. The co-substrate may at least be one $C_1$ to $C_4$ organic compound. In particular, the $C_1$ to $C_4$ co-substrate may be an energy source and may be selected from the group consisting of $C_1$ to $C_4$ alkanes, $C_1$ to $C_4$ alcohols, $C_1$ to $C_4$ aldehydes, $C_1$ to $C_4$ carboxylic acids, $C_1$ to $C_4$ carboxylic salts and mixtures thereof. More in particular, the co-substrate may at least be one $C_2$ to $C_4$ organic compound. The co-substrate may be selected from the group consisting of $C_2$ to $C_4$ alkanes, $C_2$ to $C_4$ alcohols, $C_2$ to $C_4$ aldehydes, $C_2$ to $C_4$ carboxylic acids $C_2$ to $C_4$ carboxylic salts and mixtures thereof. In particular, the co-substrate may be at least one $C_2$ to $C_4$ alkane. The $C_2$ to $C_4$ co-substrate may be branched or unbranched. In one example, the co-substrate is at least one $C_2$ to $C_4$ alcohol. The $C_2$ to $C_4$ alcohol may include monohydric alcohols, and polyhydric alcohols. The $C_1$ to $C_4$ co-substrate may be selected from the group consisting of acetate salt, acetic acid, propanoic acid, propionate salt, ethanol, propanol, ethylene glycol and glycerol. In one example, the $C_1$ to $C_4$ organic compound may be the only co-substrate used as an energy source in the aqueous medium. In this example, the aqueous medium comprises at least one $C_1$ to $C_4$ organic compound as a co-substrate and no glucose. More in particular, the aqueous medium comprises no detectable glucose.

According to any aspect of the present invention, the carbon substrate may be selected from the group consisting of alkanes, fatty alcohols, fatty aldehydes, and mixtures thereof. In particular, the carbon substrate may comprise a carbon number of 7-22. More in particular, the carbon substrate may comprise 8-22, 8-20, 8-19, 9-18, 10-22, 12-22, 10-20, 10-18, 10-16, 10-14, 7-14, or 10-12 carbon atoms. Even more in particular, the carbon substrates may be an alkane comprising, 7-22, 10-14, 7-14, or 10-12 carbon atoms.

In one aspect of the present invention, there is provided a method of producing at least one omega-hydroxyl fatty acid from at least one alkane, the method comprising:

(a) contacting the alkane with at least one yeast cell in an aqueous medium, wherein the yeast cell is capable of oxidising the alkane to the corresponding omega-hydroxyl fatty acid and the yeast cell comprises a reduced fatty acid degradation capacity; and wherein the aqueous medium comprises acetate.

In particular, the reduced fatty acid degradation capacity may be a result of:

(i) a decrease in expression relative to the wild type cell of at least one enzyme involved in the beta-oxidation pathway; and/or (ii) at least one loss-of-function mutation in at least one enzyme involved in the beta-oxidation pathway.

The acetate may be used as a co-substrate. The presence of acetate in the aqueous medium comprising the yeast cell increases the selectivity for formation of omega-hydroxyl fatty acid from alkanes. In particular, the selectivity of ω-hydroxyl fatty acid formation may be up to 70%, even up to 75%, 80%, 85%, 90%, 91%, 92%, 93%, 94%, 95%, 96%, 97%, 98%, or 99% based on the total weight of fermentation product, i.e., total weight of ω-hydroxyl fatty acid and dicarboxylic acid relative to the method in the absence of the acetate.

Therefore, the method of the present invention may be a method of producing at least one omega-hydroxyl fatty acid from at least one alkane with increased selectivity for formation of omega-hydroxyl fatty acid relative to a method where no acetate is present in the aqueous medium. In particular, in the method according to any aspect of the present invention, less by-products such as dicarboxylic acids are formed. There would thus be less waste of the starting materials making the production of omega-hydroxyl fatty acid a most cost effective process. The yield may consequently be higher and/or the more yield may be obtained in a shorter period of time. This further results in cost and time savings.

The term "acetate" as used herein, refers to both acetic acid and salts thereof, which results inevitably, because as known in the art, since the microorganisms work in an aqueous environment, there is always a balance between salt and acid present. Acetate may be used as a co-substrate in a method according to any aspect of the present invention. The ratio of molecular acetic acid to acetate is dependent upon the pH of the system, i.e., at a constant "acetate" concentration, the lower the pH, the higher the molecular acetic acid concentration relative to acetate salt.

The concentration of the co-substrate in the aqueous medium according to any aspect of the present invention may be a crucial aspect. The concentration of the co-substrate may be selected from the range between 80-800 mmol/L, 100-800, 100-700, 100-600, 100-500, 110-500, 120-500, 130-500, 140-500, 150-500, 160-500, 160-550, 160-450, 160-400, 150-350 mmol/L and the like.

In particular, the co-substrate may be acetate. The concentration of the acetate in the aqueous medium used according to any aspect of the present invention may be maintained at the specific concentrations mentioned. In particular, acetate may be present in the aqueous medium of the method according to any aspect of the present invention at a minimum concentration of at least 80 mmol/L. More in particular, the acetate concentration present in the aqueous medium may be more than or equal to about 85 mmol/L, 90 mmol/L, 95 mmol/L, 100 mmol/L, 150 mmol/L, 160 mmol/L, 170 mmol/L, 180 mmol/L, 190 mmol/L, 200 mmol/L, 250 mmol/L, 300 mmol/L, 350 mmol/L, 400 mmol/L, 450 mmol/L, 500 mmol/L, 550 mmol/L, 600 mmol/L, 650 mmol/L, 700 mmol/L, 750 mmol/L, 800 mmol/L, and the like. In one example, the concentration of acetate in the aqueous medium may be below the concentration that may result in inhibiting the oxidation capability of the yeast cell according to any aspect of the present invention. More in particular, the concentration of acetate in the aqueous medium may be more than 0 mmol/L. Even more in particular, the concentration of acetate in the aqueous medium may be at a detectable amount. The concentration of acetate in the aqueous medium may be selected from the range between 20-800 mmol/L, 30-800, 40-800, 50-800, 60-800, 70-800, 80-800, 100-800, 100-700, 100-600, 100-500, 110-500, 120-500, 130-500, 140-500, 150-500, 160-500, 160-550, 160-450, 160-400, 150-350 mmol/L and the like. In one example, the concentration of acetate in the aqueous medium may be not less than and equal to 160 mmol/l and/or not greater than and equal to 500 mmol/l.

The term 'about' as used herein refers to a variation within 20 percent. In particular, the term "about" as used herein refers to +/−20%, more in particular, +/−10%, even more in particular, +/−5% of a given measurement or value.

A skilled person would be capable of maintaining the concentration acetate at the desired level by methods known in the art. In particular, the skilled person would regularly measure the concentration of acetate in the aqueous medium and adjust the concentration of acetate accordingly by adding a higher or lower concentration of acetate into the medium. A skilled person would be capable of using any method known in the art to measure acetate concentration in an aqueous medium. For example, acetate colorimetric assay kits (Sigma-Aldrich), vacuum distillation and gas chromatography, measurements of conductivity, UV/visible spectrophotometric measurement and other methods known in the art may be used. In one example, the acetate may be measured used NMR. In particular, the concentration of acetate may be measured using semi-quantitative $^1$H-NMR spectroscopy. As an internal quantification standard sodium trimethylsilylpropionate (T(M)SP) may be used. In another example, the concentration of acetate may be measured using an enzyme kit (Article number: 10148261035) from R-Biopharm following the manufacturer's instructions. In one example, the acetate may be added to the aqueous medium in in a continuous flow separately from the continuous feed of the aqueous medium. In another example, acetate may be part of the culture medium that is being topped up. In particular, acetate may be fed to the aqueous medium as part of the nutrient feed or separately. Whichever route is taken to feed acetate to the aqueous medium, a skilled person would understand the means to maintain the concentration of acetate in the aqueous medium. In one example, the acetate concentration in the medium may be maintained by topping up the acetate every about 20 hours of fermentation. In another example, the top up of acetate in the medium may take place every about 5, 10, 15, 20, 25, 30 hours from the beginning of the culturing and/or fermentation process. In another example, the acetate may not necessarily be needed to be topped up as acetate may not be used in the method of producing omega-hydroxyl fatty acid.

In particular, acetate may be a co-substrate generating energy and reducing equivalents (NADH/NADPH/FADH) in the cell. The co-product of this reaction may be carbon dioxide. The term 'co-substrate' used herein, refers to a substrate that may be used by a multi-substrate enzyme to carry out a reaction. For example, acetate and/or ethanol may be consumed to produce energy that may be used to reduce other co-substrates such as NAD/NADP/FAD+ to produce NADH/NADPH/FADH respectively. The ethanol and/or acetate may thus be used to maintain the ratio of NAD+/NADH, NADP+/NADPH and/or FAD+/FADH in the aqueous medium or cytosol of the cell. In particular, the reaction may be as such:

Acetyl CoA+NAD+→NADH+H$_2$O+CO$_2$    REACTION 1

In one example, the concentration of acetate in the aqueous medium is maintained at any of the concentrations used according to any aspect of the present invention for 80% of the reaction period. In another example, the concentration of acetate may be maintained for 50%, 55%, 60%, 65%, 70%, 75%, 85%, 90%, 95% or 100% of the reaction time. In this regard, 'reaction time' refers to the period during with a process takes place. In particular, reaction time refers to the period of time when conversion of the carbon substrate to the desired product, omega-hydroxyl fatty acid and/or dicarboxylic acid takes place. In one example, the reaction time refers to the period of time from when a reaction starts to when the reaction ends and/or is completed, i.e. where the carbon substrate is used up. In one example, the substrate may be the alkane, and the reaction is completed when the alkane in the fermenter is used up and the reaction stops and no further alkane is fed into the fermenter. Therefore, the reaction time refers to the period from which the conversion starts (i.e. when the alkane is first converted to the desired product of omega-hydroxyl fatty acid and/or dicarboxylic acid in detectable amounts when in contact with the yeast cell in a vessel in suitable reaction conditions) to when the reaction ends (i.e. when there is no more carbon substrate such as alkane and/or when there is another limiting factor in the vessel that stops the reaction from continuing). In one example, the reaction period may be for 24 hr, 42 hr, 72 hr, 96 hr, 100 hr, 120 hrs, 150 hrs, 180 hrs, 200 hrs, 220 hrs, 240 hrs and the like. In another example, the reaction period may be for 115, 116, 117, 118, 119, 120, 121 and the like hours.

The remaining acetate from the mixture may be reused. In particular, this means that the omega-hydroxyl fatty acid formed may be allowed to accumulate and then separated by means known in the art. The remaining acetate may thus be maintained in the reaction mixture and reused. The omega-hydroxyl fatty acid may be removed in a batch-wise mode or in a continuous mode. In the latter case, the omega-hydroxyl fatty acid formed are removed continuously by a separation step known in the art.

The method according to any aspect of the present invention may comprise an earlier step for producing acetate. Acetate may be produced by any means known in the art for exogenously introducing this compound to at least the yeast cell for the production of omega-hydroxyl fatty acid. In particular, the acetate may be introduced into the aqueous medium from NaAc, HAc and/or the like.

In one example, NaAc may be fed during conversion phase and HAc may be fed by auto pH adjustment. As used herein, term "conversion phase" refers to the fermentation stage when the microorganism converts a substrate into a target fermentation product. For example, the conversion phase may refer to the fermentation stage that *Candida tropicalis* ATCC20962 converts alkanes into ω-hydroxyl fatty acids.

The conversion phase may follow a growth phase in the microorganism cell cycle. As used herein, the term "growth phase" refers to the period when microorganisms increase more rapidly in number, compared with the stationary phase in the microorganism cell cycle. The growth phase may correspond to the lag phase and exponential growth phase in the microorganism cell cycle.

Therefore, the method according to any aspect of the present invention may comprise an earlier step: a') producing yeast cells. The aim of this step may be to increase the cell number. This step may correspond to growth phase in the microorganism cell cycle. In this step, the cell may be cultured in at least one energy source such as substrates like glucose for optimum growth according to methods known in the art.

In one example, the oxidising of the carbon substrate to the corresponding omega-hydroxyl fatty acid takes place during the conversion phase of the yeast cell. No energy source may be added during the conversion phase. The co-substrate may be first added during the conversion phase. During this phase, there is almost no detectable amount of the energy source that may have been present during the growth phase of the yeast cell. The energy source may be selected from the group consisting of glucose, saccharose, fructose, acetic acid, glycerol and the like. During the conversion phase, the energy source may be at a non-detectable concentration. In particular, the concentration of the energy source may be less than 5, 0.5, 0.3, 0.2 or 0.1 mmol/L in the medium. In particular, the energy source during the growth phase may be glucose. At the conversion phase according to any aspect of the present invention, the concentration of the glucose may be lower than 20 mmol/L. In particular, the concentration of glucose may be less than 5, 0.5, 0.3, 0.2 or 0.1 mmol/L in the medium. In this example, the energy source may be different from the co-substrate according to any aspect of the present invention.

In another example, the energy source used according to any aspect of the present invention may be the same as the co-substrate used. In particular, the co-substrate used may be at least one C$_1$-C$_4$ organic compound and this may also be the energy source for the organism during the growth phase. More in particular, the energy source that may also be the co-substrate may be acetic acid, glycerol and the like.

The yeast cells according to any aspect of the present invention may be used to produce omega-hydroxyl fatty acid from all alkanes with high space-time yield, high carbon yield and high concentration in the culture supernatant. As a result of these advantages, an efficient workup may be facilitated.

The yeast cell may be capable of oxidising the alkane to the corresponding omega-hydroxyl fatty acid. This may be a naturally occurring trait in the wild type cell. The enzymes necessary for this conversion of alkanes to the corresponding omega-hydroxyl fatty acid may be part of the ω-oxidation pathway in the yeast cell. In one example, the necessary enzymes required for the conversion of the alkane to the corresponding omega-hydroxyl fatty acid may be genetically introduced into the yeast cell. The necessary enzymes required for the conversion of the alkane to the corresponding omega-hydroxyl fatty acid may be selected from the group consisting of cytochrome P450 hydroxylase complex, which consists of a cytochrome P450 monooxygenase (the CYP protein) and the accompanying NADPH cytochrome P450 reductase (NCP), fatty alcohol oxidase, fatty aldehyde dehydrogenase and the like. A skilled person would easily be able to identify the enzymes that may be introduced by recombinant means into a yeast cell to be able to carry out the conversion of an alkane to the corresponding omega-hydroxyl fatty acid. In another example, the yeast cell may naturally comprise the enzymes necessary to carry out the oxidising of an alkane to the corresponding omega-hydroxyl fatty acid.

The yeast cell may further comprise a reduced fatty acid degradation capacity. This feature of reduced fatty acid degradation capacity may be introduced by genetic modification using recombinant techniques well known in the art to the wild type cell. In one example, the wild type strain *Candida tropicalis* ATCC 20336 may be genetically modified using methods known in the art to have a reduced fatty acid degradation capacity. In particular, the cell may be modified using the method disclosed in Pictaggio, S (1992) Biotechnology, 10: 894-97 to produce ATCC20962. In another example, the wild-type yeast cell may naturally comprise a reduced/inhibited fatty acid degradation capacity. For example, the wild type yeast cell with a reduced fatty acid degradation capacity may be a strain from *Candida lipolytica*. In particular, the strain may be *Candida lipotica* 19-2 disclosed in Institute of Forestry and Pedology, Academia Sinica (1979, Acta Microbiologica Sinica, 19(1):64-70.

The phrase "wild type" as used herein in conjunction with a cell may denote a cell with a genome make-up that is in a form as seen naturally in the wild. The term may be applicable for both the whole cell and for individual genes. The term 'wild type' may thus also include cells which have been genetically modified in other aspects (i.e. with regard to one or more genes) but not in relation to the genes of interest. The term "wild type" therefore does not include such cells where the gene sequences of the specific genes of interest have been altered at least partially by man using recombinant methods. A wild type yeast cell according to any aspect of the present invention thus refers to a cell that has no genetic mutation with respect to the whole genome and/or a particular gene brought about by recombinant means. In one example, the wild type yeast cell may comprise the wild type expression of enzymes that are capable of oxidising the alkane to the corresponding omega-hydroxyl fatty acid and/or the wild type expression of relevant enzymes that result in the yeast cell comprising a reduced fatty acid degradation capacity. Therefore, in one example, a wild type cell with respect to enzyme $E_1$ may refer to a cell that has the natural/non-altered expression of the enzyme $E_1$ in the cell. The wild type cell with respect to enzymes related to fatty acid degradation may be interpreted the same way and may refer to a cell that has the natural/non-altered expression of these specific enzymes in the cell. In yet another example, the wild type cell may comprise a naturally occurring loss-of-function mutation in at least one enzyme involved in the beta-oxidation pathway. The wild-type yeast cell may thus include yeast cells that have naturally occurring mutations. These naturally occurring mutations may be in at least one enzyme involved in the beta-oxidation pathway thus resulting in the cell having reduce fatty acid degradation capacity relative to the cell without the naturally occurring mutation. The mutation of the enzyme in the wild type cell may result in a decrease in the expression of the enzyme or expression of the enzyme with no function.

In particular, the term "having a reduced fatty acid degradation capacity", as used herein, means that the respective cell degrades fatty acids, especially those taken up from the environment, at a lower rate than a wild type cell having normal fatty acid degradation capacity would under identical conditions. More in particular, the fatty acid degradation of such a cell is lower on account of deletion, inhibition or inactivation of at least one gene encoding an enzyme involved in the β-oxidation pathway. In one example, at least one enzyme involved in the β-oxidation pathway has lost 5, 10, 20, 40, 50, 75, 90 or 99% activity relative to the activity of the same enzyme under comparable conditions in the respective wild type microorganism. In another example, the yeast cell used according to any aspect of the present invention may have fatty acid degradation capacity of up to, e.g., 95, 90, 80, 70, 60, 50, 40, 30, 20, 10, 9, 8, 7, 6, 5, 4, 3, 2, 1, 0.5, 0.2, 0.1 or, 0 percent of the fatty acid degradation capacity of the wild type cell or a comparable cell.

The person skilled in the art is familiar with various techniques that may be used to delete a gene encoding an enzyme or reduce the activity of such an enzyme in a cell, for example by exposition of cells to radioactivity followed by accumulation or screening of the resulting mutants, site-directed introduction of point mutations or knock out of a chromosomally integrated gene encoding for an active enzyme, as described in Sambrook/Fritsch/Maniatis (1989).

More in particular, the fatty acid degradation capacity of a cell may be reduced in various ways. The term "deletion of a gene", as used herein, means that the nucleic acid sequence encoding the gene may be modified such that the expression of active polypeptide encoded by the gene is reduced. The expression of the enzyme may refer to the activity of the enzyme in the cell. For example, the gene may be deleted by removing in-frame a part of the sequence comprising the sequence encoding for the catalytic active centre of the polypeptide. Alternatively, the ribosome binding site may be altered such that the ribosomes no longer translate the corresponding RNA. The person skilled in the art is able to routinely measure the activity of enzymes expressed by living cells using standard assays as described in enzymology text books, for example Cornish-Bowden (1995).

Degradation of fatty acids may be accomplished by a sequence of enzymatically catalysed reactions. First of all, fatty acids are taken up and translocated across the cell membrane via a transport/acyl-activation mechanism involving at least one outer membrane protein and one inner membrane-associated protein which has fatty acid-CoA ligase activity. Inside the cell, the fatty acid to be degraded is subjected to enzymes catalysing other reactions of the β-oxidation pathway. A general description of the enzymes involved in the beta-oxidation pathway may at least be disclosed in Beopoulos, A. (2011) Appl Microbio Biotechnol, 90:1193-1206. The first intracellular step involves the conversion of acyl-CoA to enoyl-CoA through acyl-CoA dehydrogenase. The activity of an acyl-CoA dehydrogenase may be assayed using any method known in the art. For example by monitoring the concentration of NADH spectrophotometrically at 340 nm in 100 mM MOPS, pH 7.4, 0.2 mM Enoyl-CoA, 0.4 mM $NAD^+$. The resulting enoyl-CoA is converted to 3-ketoacyl-CoA via 3-hydroxylacyl-CoA through hydration and oxidation, catalysed by enoyl-CoA hydratase/3-hydroxyacyl-CoA dehydrogenase. Enoyl-CoA hydratase/3-hydroxyacyl-CoA dehydrogenase activity, more specifically formation of the product NADH may be assayed spectrophotometrically as described in the state of the art. Finally, 3-ketoacyl-CoA thiolase catalyses the cleavage of 3-ketoacyl-CoA, to give acetyl-CoA and the input acyl-CoA shortened by two carbon atoms. The activity of ketoacyl-CoA thiolase may be assayed as described in the state of the art, for example in Antonenkov, V., 1997.

In another example, the enzyme involved in the β-oxidation pathway may by recognizing the fatty acid or derivative thereof as a substrate, converts it to a metabolite formed as a part of the β-oxidation pathway. For example, the acyl-CoA dehydrogenase (EC 1.3.99.-) is an enzyme involved in the β-oxidation pathway as it interacts with fatty acid-CoA and converts fatty acid-CoA ester to enoyl-CoA, which is a metabolite formed as part of the β-oxidation. In another example, the term "enzyme involved in the β-oxidation pathway", as used herein, comprises any polypeptide from the group comprising acyl-CoA dehydrogenase (EC 1.3.99.-), enoyl-CoA hydratase (EC 4.2.1.17), 3-hydroxyacyl-CoA dehydrogenase EC 1.1.1.35) and 3-keto-acyl-CoA thiolase (EC 2.3.1.16). The acyl-CoA synthetase (EC 6.2.1.1) may catalyse the conversion of a fatty acid to the CoA ester of a fatty acid, i.e. a molecule, wherein the functional group —OH of the carboxy group is replaced with —S-CoA and introducing the fatty acid into the β-oxidation pathway. In one example, the term "acyl-CoA dehydrogenase", as used herein, may be a polypeptide capable of catalysing the conversion of an acyl-CoA to enoyl-CoA, as part of the β-oxidation pathway. The term "enoyl-CoA hydratase", as used herein, also referred to as 3-hydroxyacyl-CoA dehydrogenase, refers to a polypeptide capable of catalysing the conversion of enoyl-CoA to 3-ketoacyl-CoA through hydration and oxidation, as part of the β-oxidation pathway. The term "ketoacyl-CoA thiolase", as used herein, may refer to a polypeptide capable of catalysing the cleaving of 3-ketoacyl-CoA, resulting in an acyl-CoA shortened by two carbon atoms and acetyl-CoA, as the final step of the β-oxidation pathway.

In one example, the reduced fatty acid degradation capacity may be a result of a decrease in expression relative to the wild type cell of at least one enzyme selected from the group consisting of acyl-CoA dehydrogenase, 2,4-dienoyl-CoA reductase, enoyl-CoA hydratase, 3-ketoacyl-CoA thiolase, and acyl-coenzyme A oxidase. The reduced fatty acid degradation capacity may also be a result of loss of function of at least one enzyme selected from the group consisting of acyl-CoA dehydrogenase, 2,4-dienoyl-CoA reductase, enoyl-CoA hydratase, 3-ketoacyl-CoA thiolase, and acyl-coenzyme A oxidase. In particular, the enzyme with decreased expression and/or loss of function may be acyl-coenzyme A oxidase (EC 6.2.1.3). More in particular the acyl-coenzyme A oxidase may be selected from the group consisting of POX1, POX2, POX3, POX4, POX5 and POX6.

The reduced fatty acid degradation capacity of the yeast cell according to any aspect of the present invention may be a result of at least one loss-of function mutation in at least one of the enzymes involved in the beta-oxidation pathway as listed above. The loss-of-function mutation may be a naturally occurring phenomenon. In another example, the loss-of-function mutation may be induced by genetic means. The loss-of-function mutation occurring naturally or by artificial means may result in the cell producing the specific enzyme involved in the beta-oxidation pathway in equal amount relative to a cell without this mutation. However, the mutation in the cell may result in the cell producing a non-functional version of the enzyme. In general, loss-of-function mutations according to any aspect of the present invention may result in a strong reduction or even in a complete absence of beta oxidation. The loss-of-function mutations may be point mutations, insertions, deletions (total or partial), or gene replacement that leads to a substantial decrease in beta-oxidation. These loss-of function mutation may occur naturally or may be carried out by recombinant means.

Yeast strains in which the beta-oxidation of fatty acids may be reduced include all strains carrying at least one loss-of-function mutation in at least one gene encoding an enzyme directly involved in beta-oxidation. These strains also encompass all the strains that carry at least one loss-of-function mutation that affects beta-oxidation only indirectly, including through the biogenesis and function of peroxisomes. These cells according to any aspect of the present invention may have a combination of mutations in at least one of the enzymes involved in the beta-oxidation pathway or a combination of mutations in more than one enzyme involved in the beta-oxidation pathway. In one example, the yeast cell according to any aspect of the present invention may carry at least one loss-of-function mutation in at least one of the genes selected from the group consisting of POX1, POX2, POX3, POX4, POX5, POX6, MFE1, and POT1. This mutation may occur in the gene by natural or recombinant means.

The yeast cell used according to any aspect of the present invention may be capable of converting at least one alkane to the corresponding omega-hydroxyl fatty acid. In one example, the yeast cell according to any aspect of the present invention may have the capability of primary or monoterminal oxidation of alkanes, especially n-alkanes.

The yeast cell according to any aspect of the present invention may be selected from the group consisting of *Candida, Yarrowia, Pichia, Torulopsis, Rhodotorula*, and *Wickerhamiella*. In particular, the yeast cell may be selected from the group consisting of *Candida tropicalis, Candida cloacae, Yarrowia lipolytica, Schizosaccharomyces pombe, Rhodotorula glutinis, Wickerhamiella domercqiae* and the like.

In one example, the yeast cell has a blocked or inhibited β-oxidation pathway. This feature may be naturally present in the cell or may be introduced by genetic means known in the art. In a further example, the cell may be *Candida tropicalis* ATCC 20962, or *Yarrowia lipolytica* C122 strain with accession number CGMCC 14251 (deposited on 19 Jun. 2017 with China General Microbiological Culture Collection Center, Institute of Microbiology, Chinese Academy of Sciences, No. 1 Beichen West Road, Chaoyang District, Beijing 100101, China). *Yarrowia lipolytica* CGMCC 14251 has the following phenotype: it cannot grow in a minimum medium with alkanes (such as dodecane) or fatty acids (such as dodecanoic acid) as the sole carbon source.

In one particular example, strains derived from *Candida tropicalis* ATCC20336, like *Candida tropicalis* ATCC20962, may be used to produce ω-hydroxyl fatty acids. *Candida tropicalis* ATCC20962 is a strain in which the β-oxidation pathway is blocked by disrupting POX4 and POX5 genes encoding acyl-coenzyme A oxidase.

The enzyme used according to any aspect of the present invention may be recombinant. The term "recombinant" as used herein, refers to a molecule or is encoded by such a molecule, particularly a polypeptide or nucleic acid that, as such, does not occur naturally but is the result of genetic engineering or refers to a cell that comprises a recombinant molecule. For example, a nucleic acid molecule is recombinant if it comprises a promoter functionally linked to a sequence encoding a catalytically active polypeptide and the promoter has been engineered such that the catalytically active polypeptide is overexpressed relative to the level of the polypeptide in the corresponding wild type cell that comprises the original unaltered nucleic acid molecule.

A skilled person would be able to use any method known in the art to genetically modify a cell or microorganism. According to any aspect of the present invention, the genetically modified cell may be genetically modified so that in a defined time interval, within 2 hours, in particular within 8 hours or 24 hours, it forms at least once or twice, especially at least 10 times, at least 100 times, at least 1000 times or at least 10000 times amino acids than the wild-type cell. The increase in product formation can be determined for example by cultivating the cell according to any aspect of the present invention and the wild-type cell each separately under the same conditions (same cell density, same nutrient medium, same culture conditions) for a specified time interval in a suitable nutrient medium and then determining the amount of target product (omega hydroxyl fatty acids) in the nutrient medium.

The genetically modified cell or microorganism may be genetically different from the wild type cell or microorganism. The genetic difference between the genetically modified microorganism according to any aspect of the present invention and the wild type microorganism may be in the presence of a complete gene, amino acid, nucleotide etc. in the genetically modified microorganism that may be absent in the wild type microorganism. The cells according to any aspect of the present invention may be genetically transformed according to any method known in the art. In particular, the cells may be produced according to the method disclosed in WO2013024114.

In the same context, the phrase "decreased activity of an enzyme $E_x$" may be used interchangeably with 'decreased expression of an enzyme $E_x$" used with reference to any aspect of the present invention may be understood as meaning an activity decreased by a factor of at least 0.5, particularly of at least 0.1, more particularly of at least 0.01, even more particularly of at least 0.001 and most particularly of at least 0.0001. The phrase "decreased activity" also comprises no detectable activity ("activity of zero"). The decrease in the activity of a certain enzyme can be effected, for example, by selective mutation or by other measures known to the person skilled in the art for decreasing the activity of a certain enzyme. In particular, the person skilled in the art finds instructions for the modification and decrease of protein expression and concomitant lowering of enzyme activity by means of interrupting specific genes, for example at least in Dubeau et al. 2009. Singh & Röhm. 2008, Lee et al., 2009 and the like. The decrease in the enzymatic activity in a cell according to any aspect of the present invention may be achieved by modification of a gene comprising one of the nucleic acid sequences, wherein the modification is selected from the group comprising, consisting of, insertion of foreign DNA in the gene, deletion of at least parts of the gene, point mutations in the gene sequence, RNA interference (siRNA), antisense RNA or modification (insertion, deletion or point mutations) of regulatory sequences, such as, for example, promoters and terminators or of ribosome binding sites, which flank the gene.

Foreign DNA is to be understood in this connection as meaning any DNA sequence which is "foreign" to the gene (and not to the organism), i.e. endogenous DNA sequences can also function in this connection as "foreign DNA". In this connection, it is particularly preferred that the gene is interrupted by insertion of a selection marker gene, thus the foreign DNA is a selection marker gene, wherein preferably the insertion was effected by homologous recombination in the gene locus.

The expression of the enzymes and genes mentioned above and all mentioned below is determinable by means of 1- and 2-dimensional protein gel separation followed by optical identification of the protein concentration in the gel with appropriate evaluation software.

If the decreasing of an enzyme activity is based exclusively on decreasing the expression of the corresponding gene, then the quantification of the decreasing of the enzyme activity can be simply determined by a comparison of the 1- or 2-dimensional protein separations between wild type and genetically modified cell. A common method for the preparation of the protein gels with bacteria and for identification of the proteins is the procedure described by Hermann et al. (Electrophoresis, 22: 1712-23 (2001). The protein concentration can also be analysed by Western blot hybridization with an antibody specific for the protein to be determined (Sambrook et al., Molecular Cloning: a laboratory manual, 2nd Ed. Cold Spring Harbor Laboratory Press, Cold Spring Harbor, N.Y. USA, 1989) followed by optical evaluation with appropriate software for concentration determination (Lohaus and Meyer (1989) Biospektrum, 5: 32-39; Lottspeich (1999), Angewandte Chemie 111: 2630-2647). This method is also always an option when possible products of the reaction to be catalysed by the enzyme activity to be determined may be rapidly metabolized in the microorganism or else the activity in the wild type is itself too low for it to be possible adequately to determine the enzyme activity to be determined on the basis of the production formation.

The accession numbers stated in connection with the present invention mentioned throughout this specification correspond to the NCBI ProteinBank database entries with the date 26 Jul. 2011; as a rule, the version number of the entry is identified here by "numerals" such as for example "0.1".

All stated percentages (%) are, unless otherwise stated, mass percent.

Alkanes are saturated hydrocarbons that have various applications depending on the number of carbon atoms and on the structure of the alkane (i.e. branched, linear, cyclic etc.). Alkanes (technically, always acyclic or open-chain compounds) have the general chemical formula $C_nH_{2n+2}$. The alkane used according to any aspect of the present invention may be an unsubstituted alkanes having 3 to 22, 6 to 18, or 8 to 14, carbon atoms. In particular, the alkane may be unbranched. More in particular, the alkane may be selected from the group consisting of octane, decane, dodecane and tetradecane. Even more in particular, the alkane used according to any aspect of the present invention may comprise at least 6 C atoms. In particular, the alkane may be selected from the group consisting of $C_7$-$C_{22}$ alkanes. More in particular, the alkane may be selected from the group consisting of $C_8$-$C_{22}$, $C_8$-$C_{20}$, $C_8$-$C_{18}$, $C_5$-$C_{18}$, $C_{10}$-$C_{20}$, $C_{10}$-$C_{18}$, $C_{10}$-$C_{16}$, $C_{10}$-$C_{14}$, $C_{10}$-$C_{12}$ alkanes and the like. Even more in particular, the alkane may be selected from the group consisting of $C_{10}$-$C_{12}$ alkanes and the like. In one example, the alkane used according to any aspect of the present invention may be selected from the group consisting of decane, undecane, dodecane and the like.

The selectivity of ω-hydroxyl fatty acid of the method according to any aspect of the present invention may be up to 70%, even up to 75%, 80%, 85%, 90%, 91%, 92%, 93%, 94%, 95%, 96%, 97%, 98%, or 99% based on the total weight of fermentation product, i.e., total weight of ω-hydroxyl fatty acid and dicarboxylic acid.

Therefore, the method according to any aspect of the present invention provides a simple and effective means to achieve the selective production of ω-hydroxyl fatty acids by fermentation from alkanes using simple microorganisms such as yeast cells, in particular *Candida tropicalis* or *Yarrowia lipolytica*. No tedious genetic modification may be required. The dominant product may be selected to be ω-hydroxyl fatty acids instead of dicarboxylic acids.

The term "contacting", as used herein, means bringing about direct contact between the cell according to any aspect of the present invention and the medium comprising the alkane and/or acetate in step (a). For example, the cell, and the medium comprising the alkane and/or acetate may be in different compartments in step (a). In particular, the alkane may be in a gaseous state and added to the medium comprising the cells according to any aspect of the present invention.

The method according to any aspect of the present invention may be a batch culture, fed batch culture or semi-continuous fermentation. In one example, the method is a fed batch culture. According to any aspect of the present invention, the fermentation may be conducted under aerated cultivation conditions.

The process of the present invention has no special requirement to fermentation conditions like medium, pH value or fermentation time, these can all be conventional. In one example, the method according to any aspect of the present invention may be carried out in an aqueous medium with a pH between 5 and 8, 5.5 and 7. The pressure may be between 1 and 10 bar.

The term "an aqueous solution" or "medium" comprises any solution comprising water, mainly water as solvent that may be used to keep the cell according to any aspect of the present invention, at least temporarily, in a metabolically active and/or viable state and comprises, if such is necessary, any additional substrates. The person skilled in the art is familiar with the preparation of numerous aqueous solutions, usually referred to as media that may be used to keep the cells. It is advantageous to use as an aqueous solution a minimal medium, i.e. a medium of reasonably simple composition that comprises only the minimal set of salts and nutrients indispensable for keeping the cell in a metabolically active and/or viable state, by contrast to complex mediums, to avoid dispensable contamination of the products with unwanted side products. For example, M9 medium may be used as a minimal medium. The cells are incubated with the carbon source sufficiently long enough to produce the desired product. For example for at least 1, 2, 4, 5, 10 or 20 hours. The temperature chosen must be such that the cells according to any aspect of the present invention remains catalytically competent and/or metabolically active, for example 10 to 42° C., preferably 30 to 40° C., in particular, 32 to 38° C.

Means of extracting omega-hydroxyl fatty acid according to any aspect of the present invention may include an aqueous two-phase system for example comprising polyethylene glycol, capillary electrolysis, chromatography and the like. In one example, when chromatography is used as the means of extraction, ion exchange columns may be used. In another example, amino acids may be precipitated using pH shifts. A skilled person may easily identify the most suitable means of extracting omega-hydroxyl fatty acids by simple trial and error.

According to another aspect of the present invention, there is provided a use of a yeast cell to produce at least one omega-hydroxyl fatty acid from at least one alkane in an aqueous medium, wherein the yeast cell comprises a reduced fatty acid degradation capacity; and the aqueous medium comprises acetate used as a co-substrate.

According to a further aspect of the present invention, the omega-hydroxyl fatty acid produced according to any aspect of the present invention may be used as a raw material for polyamide, in particular polyamide-12 production. In particular, the methods disclosed in WO/2009/077461 may be used to selectively produce polyamide12 from the omega-hydroxyl fatty acid produced according to any aspect of the present invention.

According to one aspect of the present invention, there is provided a method of producing a polyamide, comprising:
(i) converting the omega-hydroxyl fatty acid produced according to any aspect of the present invention to at least one omega-amino hydroxyl fatty acid by any means known in the art, and
(ii) using the omega-amino hydroxyl fatty acid as a monomer for polymerisation to produce the polyamide.

According to yet another aspect of the present invention, there is provided a use of at least one $C_1$ to $C_4$ organic compound to increase selectivity of formation of omega-hydroxyl fatty acid from at least one carbon substrate during a fermentation process wherein the process comprises:
(a) contacting the carbon substrate with at least one yeast cell in an aqueous medium, wherein the yeast cell is capable of oxidising the carbon substrate to the corresponding omega-hydroxyl fatty acid and/or dicarboxylic acid; and the yeast cell comprises a reduced fatty acid degradation capacity, wherein the aqueous medium comprises at least one $C_1$ to $C_4$ organic compound. In particular, the $C_1$ to $C_4$ organic compound is an acetate.

In summary, the omega-hydroxyl fatty acid may further be converted to omega-oxocarboxylic acids and then to omega-aminocarboxylic acid which will then be converted to polyamides by polymerisation. A skilled person would be capable of finding a suitable technique for these conversions based on the methods known in the art. In one example, further enzymes such as an alkane monooxygenase, an alcohol dehydrogenase, or an alcohol oxidase may be introduced into the cell according to any aspect of the present invention for converting the omega-hydroxyl fatty acid to omega-oxocarboxylic acid. The cell may also express at least one ω-transaminase to convert the omega-oxocarboxylic acid to omega-aminocarboxylic acid. In another example, the omega-hydroxyl fatty acid produced according to any aspect of the present invention may be introduced to a further cell capable of converting the omega-hydroxyl fatty acid to omega-aminocarboxylic acid.

EXAMPLES

The foregoing describes preferred embodiments, which, as will be understood by those skilled in the art, may be subject to variations or modifications in design, construction or operation without departing from the scope of the claims. These variations, for instance, are intended to be covered by the scope of the claims.

Methods and Materials

In the examples, the identification of fermentation products was conducted by using GC-MS and the amount of the fermentation products were determined via Gas Chromatography-Flame Ionization Detection (GC-FID).

The samples of fermentation products were treated by TMS (trimethyl-silylation) derivatization before injection for GC-FID analysis.

The detailed procedure is as follows: sample was dissolved in ethyl acetate or acetonitrile (if necessary), then the solution was mixed with derivatization reagent (N,O-bis(trimethylsilyl)trifluoroacetamide, BSTFA) by 1:1 (v/v) in the 2 mL vial (80 uL: 80 uL in the 300 uL insert vial). Afterwards, the mixtures were heated to 80° C. in the oven for 30 min before injection to GC-FID analysis.

Instrument: Agilent 7890B;
Inlet conditions: Temperature: 260° C., Split ratio: 20:1;
Injection Volume: 1 uL;
Column: Agilent 19091J-413L, HP5, 30 m×320 um×0.25 um;
Carrier gas: Helium;
Column flow: constant, 1 mL/min;
Oven Program: 60° C. (hold 1 min), 10° C./min to 300° C. (hold 5 min);
FID detector:
 Temperature: 280° C.;
 Air flow: 300 mL/min;
 $H_2$ Fuel flow: 30 mL/min;
 Makeup flow: 25 mL/min.

Example 1

Seed Culture Phase:

Colonies on agar plate of *Candida tropicalis* ATCC20962 strain were precultured in 100 mL seed medium and shaken at 200 rpm, 30° C. for 20 h in 1 L baffled shaking flask.

Seed medium contains (per liter): glucose, 30 g; corn steep liquor (Sigma), 9 g; $KH_2PO_4$, 2 g; $K_2HPO_4$, 1 g; MgSO4, 1.0 g; $CaCl_2$, 0.1 g; NaCl, 0.1 g; urea, 3.6 g; and 1 mL/L of a trace elements solution (per liter: $H_3BO_3$, 0.5 g; $CuSO_4.5H_2O$, 0.04 g; KI, 0.1 g; $FeCl_3.6H_2O$, 0.6 g; $MnSO_4.H_2O$, 0.4 g; $Na_2MoO_4.2H_2O$, 0.2 g; $ZnSO_4.7H_2O$, 0.4 g).

Growth Phase:

The cells were inoculated at 10% (v/v) into 400 mL of growth medium in a 1.4 L DASGIP fermenter (DASGIP Parallel Bioreactor Systems for Microbial Research and Development, 1 L working volume). 30 g/L decane was added to induce the expression of related enzymes such as cytochrome P450 (He, F., (2005), Yeast, 22:481-491; Van Beillen, J. B., (2006), App and Env. Microbiology:59-65 and Kogure T. (2007), FEMS Microbiol Lett: 106-111). The culture was grown at 30° C. at an aeration rate of 1.0 wm for 30 hrs as growth phase. The pH was maintained at 5.80 by automatic addition of 4 mol/L NaOH or 5 mol/L HCl solutions. Dissolved oxygen was maintained at 25% saturation by agitation and $O_2$-cascade control mode. After 6 h growth, glucose (600 g/L) was fed exponentially based on the equation below, wherein $\rho = 0.05 \ h^{-1}$ and $Y_{X/S} = 0.35$ g DCW (dry cell weight)/g glucose and $m_s = 0.04$ g/g DCW*h. $C_{s0}$ is substrate concentration, $C_{X0}$ is DCW at the beginning of the feeding.

$$F_f(Feedrate) = \left(\frac{\mu}{Y_{X/S}} + m_S\right) \cdot \frac{c_{X0} \cdot V_0 \cdot e^{\mu t}}{c_{S0}}$$

Growth medium contains (per liter): glucose, 30 g; $(NH_4)_2SO_4$, 8 g; corn steep liquor (Sigma), 9 g; $KH_2PO_4$, 2 g; $K_2HPO_4$, 1 g; MgSO4, 1.0 g; $CaCl_2$, 0.1 g; NaCl, 0.1 g; antifoam 204 (Sigma Lot #: MKBP4191V), 1 mL and 1 mL/L of a trace elements solution (per liter: $H_3BO_3$, 0.5 g; $CuSO_4.5H_2O$, 0.04 g; KI, 0.1 g; $FeCl_3.6H_2O$, 0.6 g; $MnSO_4.H_2O$, 0.4 g; $Na_2MoO_4.2H_2O$, 0.2 g; $ZnSO_4.7H_2O$, 0.4 g).

Conversion Phase:

Conversion of decane started after 30 hrs of growth phase. pH was raised to 7.5 gradually in 2 hrs with 4 mol/L NaOH solution. Decane was fed in a rate of 0.4 mL/h and NaAc (300 g/L, pH7.5) was fed in a rate of 1.0-2.0 mL/h (the concentration of $Ac^-$ was from 10 g/L to 30 g/L). Then pH was maintained at 7.5 by automatic addition of 75% (v/v) HAc. Conversion phase lasted for 130 hrs. Broth samples were taken at intervals to determine cell density, residual glucose, $Ac^-$ concentrations and products concentrations.

The concentration of residual glucose was detected enzymatically (glucose oxidase) and the concentration was not detectable.

The concentration of acetic group ($Ac^-$) was quantified by H-NMR method which calculated samples against the internal standard (TMSP, 3-(trimethylsilyl)propionic-2,2,3,3-d4 acid sodium salt) with known concentration. The concentration of Ac— was from 10 g/L to 30 g/L.

Figure 2:
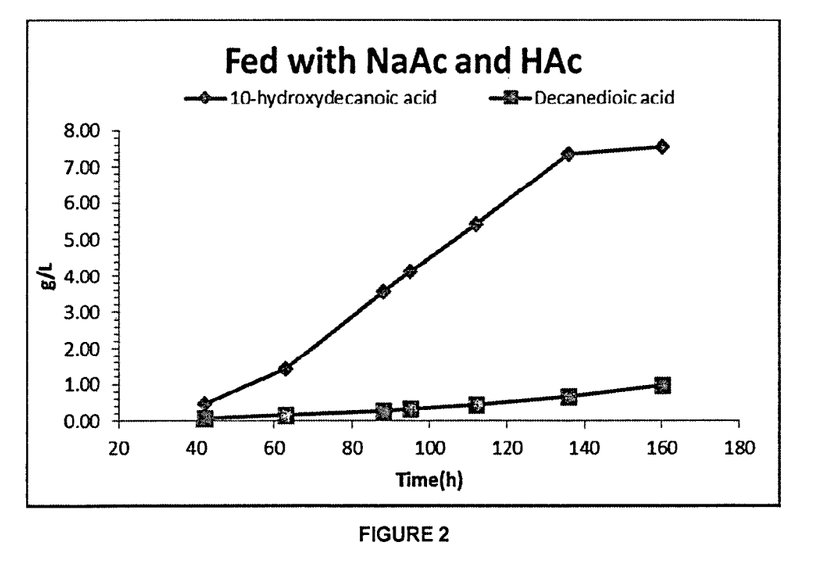
FIG. 2 is a graph of the concentrations of 10-hydroxydecanoic acid and decanedioic acid over time when fed with NaAc and HAc according to Example 1.

The concentrations of 10-hydroxydecanoic acid and decanedioic acid over time when fed with NaAc and HAc are shown in FIG. 2.

Sample Extraction:

200 uL sample broth was acidified to pH 1-2 by adding 5M HCl, then 8-fold (1.6 mL) ethyl acetate (EA) was added. After shaking vigorously, EA phase was taken by centrifugation for 2 min under 25° C., 13000 rpm. Then 1 mL of EA phase was used for GC-FID analysis to determine the oxidized products (10-hydroxydecanoic acid and decanedioic acid) in broth.

Comparative Example 1

Seed culture phase and growth phase were performed as those in Example 1. In conversion phase, conversion of decane started after 30 hrs of growth phase. pH was raised to 7.5 gradually in 2 hrs with 4 mol/L NaOH solution. Decane was fed in a rate of 0.4 mL/h and glucose (600 g/L) was fed in a rate that kept the concentration of glucose at around 10 g/L. Then pH was maintained at 7.5 by automatic addition of 4 mol/L NaOH solution. Conversion phase lasted for 130 hrs. Broth samples were taken at intervals to determine cell density, residual glucose, and products concentrations.

Figure 1:
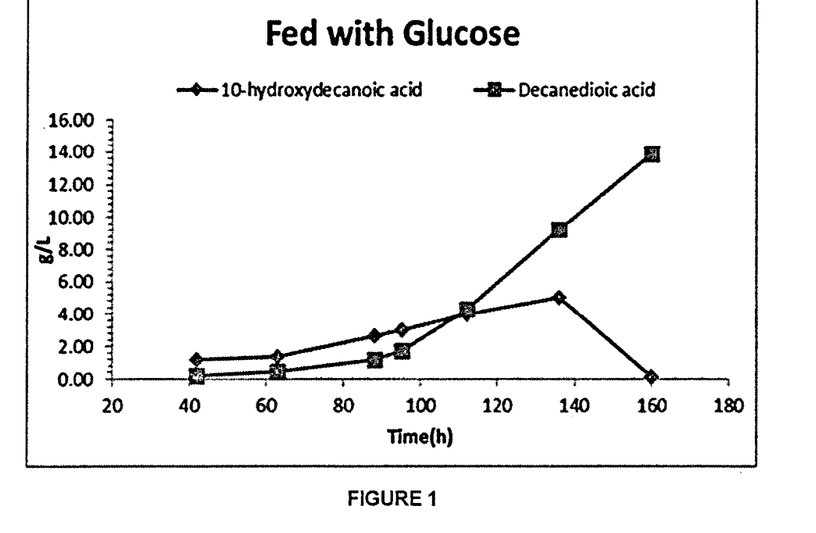
FIG. 1 is a graph of the concentrations of 10-hydroxydecanoic acid and decanedioic acid over time when fed with glucose according to Comparative Example 1.

As shown in FIG. 1, when glucose was fed in conversion phase according to comparative example 1, the main product was decanedioic acid, whose concentration was 13.88 g/L at 160 h, and nearly no 10-hydroxydecanoic acid was found (0.15 g/L). The selectivity of 10-hydroxydecanoic acid was 1.1%.

However, as shown in FIG. 2, when NaAc and HAc was fed in conversion phase according to Example 1, the dominant product was 10-hydroxydecanoic acid rather than decanedioic acid (7.56 g/L 10-hydroxydecanoic acid vs 0.96 g/L decanedioic acid at 160 h). The selectivity of 10-hydroxydecanoic acid was 88.7%.

Example 2

Seed culture phase and growth phase were performed as those in Example 1. Then the induced cells were collected by centrifugation for 4 min at 4500 rpm, 4° C. Further, the collected cells were washed by 10 mM PBS (phosphate buffered saline, pH7.5) to obtain resting cells.

An aliquot of the resting cells was suspended in medium containing NaAc (28 g/L) and alkane substrate (10 g/L) in 25 mL 10 mM PBS (pH7.5) to make a cell suspension of OD10. This cell suspension was used in conversion phase. Three alkanes: decane, undecane and dodecane, were tested as substrate, respectively. The conversion phase was conducted in 250 mL Schott baffled shaking flasks, in which air was replaced by pure oxygen, for 24 hrs under 30° C. and 200 rpm. The products in broth was extracted with equal amount of ethyl acetate after acidification. The quantification of concentration of each product was determined by GC-FID. After 24 hr of conversion, the residual NaAc concentration was about 2-3 g/L.

Figure 3:
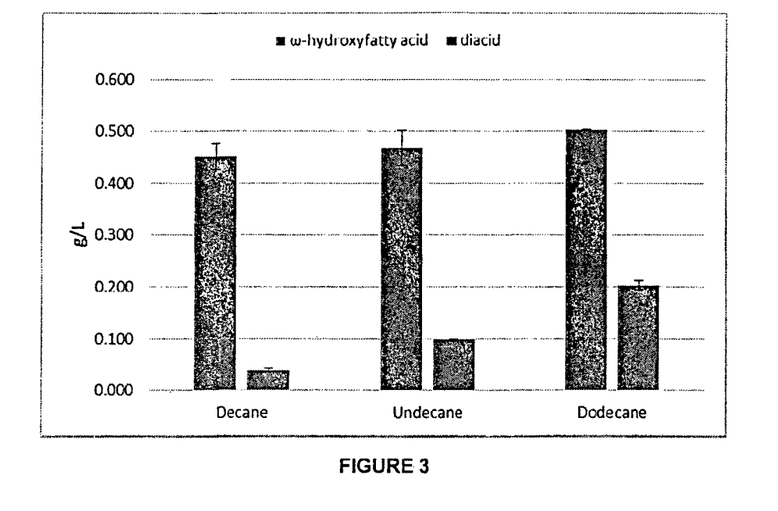
FIG. 3 is a graph of the concentrations of ω-hydroxyl fatty acids and dicarboxylic acids using different alkane substrates according to Example 2.

The results in FIG. 3 showed that for all these three substrates, the main products were all ω-hydroxyl fatty acids. The concentration of 10-hydroxydecanoic acid and decanedioic acid was 0.452 g/L and 0.039 g/L, respectively, and the selectivity of 10-hydroxydecanoic acid was 92.0%. The concentration of 11-hydroxyundecanoic acid and undecanedioic acid was 0.469 g/L and 0.098 g/L, respectively, and the selectivity of 11-hydroxyundecanoic acid was 82.7%. The concentration of 12-hydroxydodecanoic acid and dodecanedioic acid was 0.502 g/L and 0.204 g/L, respectively, and the selectivity of 12-hydroxydodecanoic acid was 71.1%.

Example 3

Seed Culture Phase:
Colonies on agar plate of *Yarrowia lipolytica* C122 strain with accession number CGMCC 14251 (deposited on 19 Jun. 2017 with China General Microbiological Culture Collection Center, Institute of Microbiology, Chinese Academy of Sciences, No. 1 Beichen West Road, Chaoyang District, Beijing 100101, China) were precultured in 50 mL seed medium and shaken at 200 rpm, 30° C. for 24 h in 500 mL baffled shaking flask.

Seed medium contains (per liter): glucose, 10 g; peptone, 20 g; yeast extract, 10 g; decane, 3 g.

Then the induced cells were collected by centrifugation for 4 min at 4500 rpm, 4° C. Further, the collected cells were washed by 10 mM PBS (phosphate buffered saline, pH7.5) to obtain resting cells.

An aliquot of the resting cells was suspended in medium containing NaAc (28 g/L) and alkane substrate (40 g/L) in 25 mL 10 mM PBS (pH7.5) to make a cell suspension of OD20. This cell suspension was used in conversion phase. Decane was tested as alkane substrate.

Conversion Phase:
The conversion phase was conducted in 250 mL Schott baffled shaking flasks, in which air was replaced by pure oxygen, for 24 hrs under 30° C. and 200 rpm. The products in broth were extracted with equal amount of ethyl acetate after acidification. The quantification of concentration of each product was determined by GC-FID.

Figure 4:
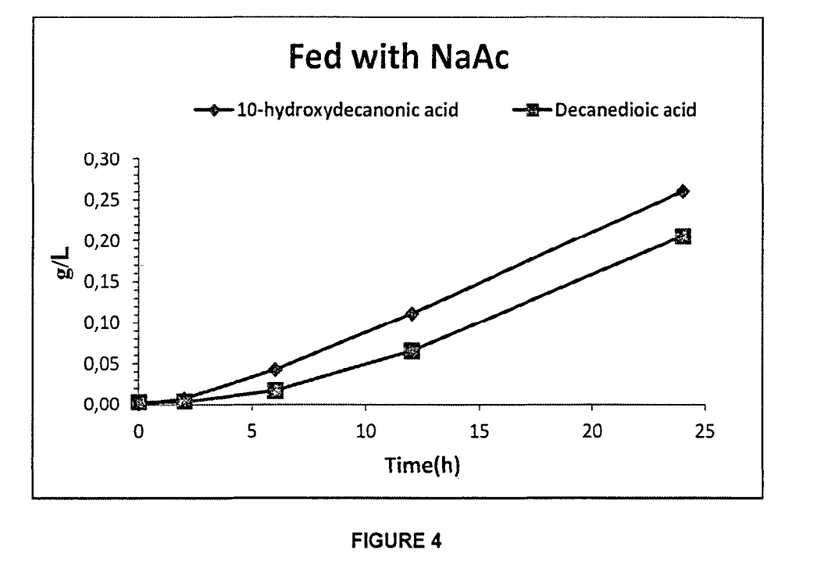
FIG. 4 is a graph of the concentrations of 10-hydroxydecanoic acid and decanedioic acid over time when fed with NaAc according to Example 3.

FIG. 4 is a graph of the concentrations of 10-hydroxydecanoic acid and decanedioic acid over time when fed with NaAc according to Example 3. The results in FIG. 4 showed that the main product was w-hydroxyl fatty acid. The concentration of 10-hydroxydecanoic acid was 0.260 g/L, and the selectivity of 10-hydroxydecanoic acid was 58.3%.

Comparative Example 3

Seed culture phase and conversion phase were performed as those in Example 3, except that in conversion phase, NaAc was replaced by glucose (20 g/L).

Figure 5:
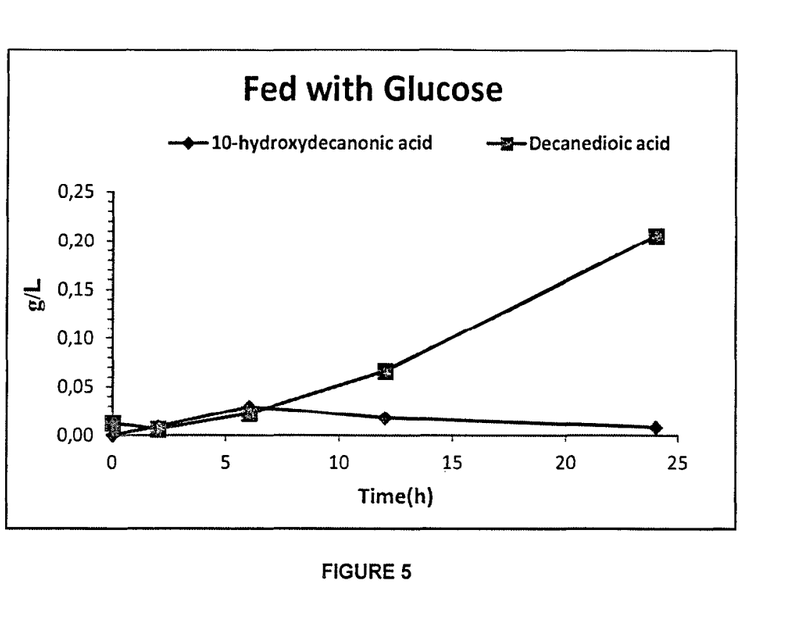
FIG. 5 is a graph of the concentrations of 10-hydroxydecanoic acid and decanedioic acid over time when fed with glucose according to Comparative Example 2.

The results in FIG. 5 showed that the main product was decanedioic acid. The concentration of decanedioic acid was 0.205 g/L, and the selectivity of 10-hydroxydecanoic acid was 4.0%.

The invention claimed is:

1. A method of producing at least one omega-hydroxyl fatty acid, the method comprising:
   contacting at least one alkane with at least one yeast cell in an aqueous medium,
   wherein the at least one yeast cell is selected from the group consisting of *Candida tropocalis* with accession number ATCC20962 and *Yarrowia lipolytica* C122 strain with accession number CGMCC14251, and is capable of oxidizing the at least one alkane to a corresponding omega-hydroxyl fatty acid and the at least one yeast cell comprises a reduced fatty acid degradation capacity;
   the reduced fatty acid degradation capacity is a result of:
   (i) a decrease in expression relative to a wild type cell of at least one enzyme involved in a beta-oxidation pathway; and/or
   (ii) at least one loss-of-function mutation in at least one enzyme involved in the beta-oxidation pathway; and
   the aqueous medium comprises acetate as a co-substrate such that an acetate concentration of the aqueous medium is at least 20 mmol/L, and has a non-detectable concentration of glucose.

2. The method according to claim 1, wherein the acetate concentration is at least 80 mmol/L.

3. The method according to claim 1, wherein the acetate concentration is maintained between 80-800 mmol/L during the contacting.

4. The method according to claim 1, wherein the acetate concentration is maintained between 160-500 mmol/L during the contacting.

5. The method according to claim 1, wherein the acetate is selected from the group consisting of NaAc and HAc.

6. The method according to claim 1, wherein the at least one alkane comprises at least 6 carbon atoms.

7. The method according to claim 1, wherein the at least one alkane is selected from the group consisting of $C_7$-$C_{22}$ alkanes.

8. The method according to claim 1, wherein the at least one alkane is selected from the group consisting of $C_{10}$-$C_{12}$ alkanes.

9. The method according to claim 1, wherein the at least one yeast cell is *Candida tropocalis* with accession number ATCC20962.

10. The method according to claim 1, wherein the at least one yeast cell is *Yarrowia lipolytica* C122 strain with accession number CGMCC14251.

11. The method according to claim 1, wherein the reduced fatty acid degradation capacity is a result of a decrease in expression relative to the wild type cell of the at least one enzyme selected from the group consisting of acyl-CoA dehydrogenase, 2,4-dienoyl-CoA reductase, enoyl-CoA hydratase and 3-ketoacyl-CoA thiolase.

12. The method according to claim 1, wherein the at least one alkane is selected from the group consisting of octane, decane, undecane, dodecane, and tetradecane.

13. The method according to claim 1, wherein the at least one alkane is selected from the group consisting of decane, undecane, and dodecane.

14. The method according to claim 1, wherein the contacting is performed such that the at least one omega-hydroxyl fatty acid and a dicarboxylic acid are produced, and that an amount of the at least one omega-hydroxyl fatty acid is larger than an amount of the dicarboxylic acid.

15. The method according to claim 14, wherein a selectivity of the at least one omega-hydroxyl fatty acid is at least 58.3%, where the selectivity is a ratio of the amount of the at least one omega-hydroxyl fatty acid to a total amount of the at least one omega-hydroxyl fatty acid and the amount of the dicarboxylic acid.

16. The method according to claim 13, wherein the contacting is performed such that the at least one omega-hydroxyl fatty acid and a dicarboxylic acid are produced, and that an amount of the at least one omega-hydroxyl fatty acid is larger than an amount of the dicarboxylic acid.

17. The method according to claim 16, wherein a selectivity of the at least one omega-hydroxyl fatty acid is at least 58.3%, where the selectivity is a ratio of the amount of the at least one omega-hydroxyl fatty acid to a total amount of the at least one omega-hydroxyl fatty acid and the amount of the dicarboxylic acid.

* * * * *